US010080811B2

(12) United States Patent
Saha et al.

(10) Patent No.: US 10,080,811 B2
(45) Date of Patent: Sep. 25, 2018

(54) DIAGNOSTIC MARKER COMPOUNDS AND THEIR USE

(71) Applicant: University of Leeds, Leeds, Yorkshire (GB)

(72) Inventors: Sikha Saha, Leeds (GB); Gin Jose, Leeds (GB); Animesh Jha, Leeds (GB)

(73) Assignee: University of Leeds, Yorkshire (GB)

( * ) Notice: Subject to any disclaimer, the term of this patent is extended or adjusted under 35 U.S.C. 154(b) by 283 days.

(21) Appl. No.: 14/382,728

(22) PCT Filed: Mar. 7, 2013

(86) PCT No.: PCT/GB2013/050560
§ 371 (c)(1),
(2) Date: Sep. 3, 2014

(87) PCT Pub. No.: WO2013/132252
PCT Pub. Date: Sep. 12, 2013

(65) Prior Publication Data
US 2015/0045664 A1    Feb. 12, 2015

(30) Foreign Application Priority Data

Mar. 7, 2012 (GB) .................................. 1204014.3

(51) Int. Cl.
A61B 5/1455 (2006.01)
A61K 49/00 (2006.01)
A61B 5/00 (2006.01)
A61K 47/52 (2017.01)

(52) U.S. Cl.
CPC ........ *A61K 49/0019* (2013.01); *A61B 5/0059* (2013.01); *A61B 5/1455* (2013.01); *A61K 47/52* (2017.08); *A61K 49/0004* (2013.01)

(58) Field of Classification Search
CPC ... A61B 5/0059; A61B 5/1455; A61B 5/0071; G01N 21/6428
See application file for complete search history.

(56) References Cited

U.S. PATENT DOCUMENTS 8,372,435 B2 *  2/2013  Schwartz ............. G01N 33/533
                                                 420/416
2007/0037224 A1 *  2/2007  Hamer ............. G01N 33/57488
                                                 435/7.21
2011/0237942 A1 *  9/2011  Zako .................... A61B 5/0077
                                                 600/431
2011/0287558 A1 * 11/2011  Parker ................... G01N 33/52
                                                 436/501
2012/0171115 A1 *  7/2012  Hudson .............. A61K 49/0002
                                                 424/1.49

FOREIGN PATENT DOCUMENTS

WO    WO 2007/113386 A1    10/2007
WO    WO 2010/031471 A1     3/2010

OTHER PUBLICATIONS

Aime, S. et al., "Separation of Intra-and Extracellular Lactate NMR Signals Using a Lanthanide Shift Reagent", *Magnetic Resonance in Medicine*, 47:10-13 (2002).
Amaral, E.C.C. et al., "Glutarates and Perfluoroglutarates of Rare Earths and Yttrium-I", *J. inorg.nucl.Chem.*, 31: 2695-2704 (1969).
Badari, Alessandra, "Chiral Lanthanide Complexes as Probes for Bioactive Species", *University of Durham*, 204 pages (2005).
International Search Report for International Application No. PCT/GB2013/050560 "Diagnostic Marker Compounds and their Use", dated Sep. 12, 2013.
Pal, R. et al., "A europium luminescence assay of lactate and citrate in biological fluids", *Organic & Biomolecular Chemistry*, 7: 1525-1528 (2009).
Sturzu, A., et al., "Cellular uptake of cationic gadolinium-DOTA peptide conjugates with and without N-terminal myristoylation", *Amino Acids* 37:249-255 (2009).
Tian, G. et al., "Complexation of Lactate with Neodymium (III) and Europium (III) at Variable Temperatures: Studies by Potentiometry, Microcalorimetry, Optical Absorption, and Luminescence Spectroscopy", *American Chemical Society*, 49: 10598-10605 (2010).

* cited by examiner

*Primary Examiner* — Eric Winakur
(74) *Attorney, Agent, or Firm* — Hamilton, Brook, Smith & Reynolds, P.C.

(57) ABSTRACT

The present Invention relates to the monitoring of biological substances, such as non-invasive monitoring of such substances in animal, for examples biomarkers and metabolites. Specifically, the invention further relates to such monitoring using rare earth tagged marker compounds. The invention further relates to such monitoring using laser spectroscopy or Raman spectroscopy. The invention further relates to the use of such monitoring in disease states, such as stroke, neurological disorders and cardiovascular disorders. The invention further relates to novel rare-earth conjugated marker compounds and processes for preparing said rare-earth conjugated compounds

16 Claims, 12 Drawing Sheets

DIAGNOSTIC MARKER COMPOUNDS AND THEIR USE

The present invention relates to the monitoring of biological substances, for examples non-invasive monitoring in animals, such as monitoring biomarkers, metabolites, proteins, enzymes and cytokines. Specifically, the invention further relates to such monitoring using rare earth metal-conjugated marker compounds. The invention further relates to such monitoring using spectroscopic methods, such as laser spectroscopy or Raman spectroscopy. The invention further relates to the use of such monitoring in disease states, such as cardiovascular, microvascular and macrovascular diseases, neuropsychiatric diseases, neurological diseases and cancer. The invention further relates to novel rare-earth metal-conjugated marker compounds and processes for their preparation.

Cardiovascular diseases and stroke and related neurological diseases are the major causes of death and long-term disability throughout the world. As major risk factors, atherosclerosis and diabetes contribute substantially to these medical conditions. Although MRI, CAT scans and ultrasound are used at major hospitals for imaging and are supplemented by NMR, FT-IR or mass spectroscopy for chemical analysis, they are not suitable for the "point-of-care" where the early diagnosis may benefit primary prevention and treatment of these diseases. At present there is no easily accessible diagnosis for warning potential patient population which enables identification of onset and occurrence of these diseases. The poor prognosis of patients suffering from stroke, cardiac ischemia or cancer results from the lack of early diagnosis and effective therapies.

We have developed laser-based methods for analysis of biomarkers in disease conditions such as cardiovascular, stroke and neuronal diseases. One approach is based on non-invasive trans-cutaneous measurement, for example using laser spectroscopy, of metabolites/enzymes which have been conjugated with rare-earth metals for enabling strong signal generation for transcutaneous analysis for example, when excited with an external laser source thus providing novel pathways for non-invasive detection and imaging through skin.

In a first embodiment there is provided a method for the measurement of one or more metabolites in an animal comprising the measurement of a rare earth metal-conjugated marker.

In a further aspect of the first embodiment there is provided a method for the measurement of a disease condition comprising the measurement of a rare earth metal-conjugated marker.

In the first embodiment measurement may be made in vivo or in a sample of biological material obtained from said animal. Examples of samples of biological material include blood, serum, urine, biopsied material etc.

In a further embodiment there is provided a method for the non-invasive measurement of one or more metabolites in an animal comprising the measurement of a rare earth metal-conjugated marker.

In a further embodiment there is provided a method for the non-invasive measurement of a disease condition comprising the measurement of a rare earth metal-conjugated marker.

In a further embodiment there is provided a method for the continuous in-vivo non-invasive measurement of one or more metabolites in an animal comprising the measurement of a rare earth metal-conjugated marker.

In a further embodiment there is provided for the continuous in-vivo non-invasive measurement of a disease condition comprising the measurement of a rare earth metal-conjugated marker.

Non-invasive measurements can be made at any point of an animal suitable for excitation and detection of the rare earth metal-conjugated marker, for example points adjacent to a blood vessel such as superficial blood vessels or the carotid artery or adjacent to organs of the animal body.

For the avoidance of doubt the measurement of a disease condition includes the detection and/or the measurement of the progression of and/or predicting the risk of developing such a disease condition.

For the avoidance of doubt in methods of the invention one or more rare earth conjugated marker may be use to measure one or more metabolites. Where more than one metabolites is measured markers may be conjugated to different rare earth metals to aid in resolving different metabolites.

Disease conditions comprise any disease condition for which a rare-earth tagged marker facilitates the detection and/or measurement of the progression of and/or predicting the risk of a disease. In one embodiment the disease condition is selected from: cardiovascular diseases, neuropsychiatric diseases, neurological diseases and cancer.

Cardiovascular disease (CVD) is used to classify numerous conditions that affect the heart, heart valves, blood, and vasculature of the body, including coronary artery disease (CAD). Cardiovascular diseases include endothelial dysfunction, coronary artery disease, carotid artery disease, angina pectoris, myocardial infarction, atherosclerosis, congestive heart failure, hypertension, cerebrovascular disease, stroke, transient ischemic attacks, deep vein thrombosis, peripheral artery disease, cardiomyopathy, arrhythmias, aortic stenosis, and aneurysm. Such diseases frequently involve atherosclerosis.

Examples of neurological diseases include: Alzheimer's disease, mild cognitive impairment, dementia, age-related cognitive decline, stroke, traumatic brain injury, spinal cord injury. Examples of neuropsychiatric diseases including depression, anxiety, schizophrenia and the like and conditions which show nerve cell dysfunction leading to cognitive, behavioral, and mood disorders.

Markers conjugated to rare earth metals are suitable for measurement in-vitro and in-vivo in most animal tissues and body fluids. Examples include brain tissue such as brain homogenates and brain tumour tissue, cerebrospinal fluid, ischemic tissue such as ischemic cardiac tissue, ischemic optic nerve and ischemic artery, vein and blood vessels, atherosclerotic tissue, cancer tissue, blood, urine.

Methods of the invention can be used to measure both large molecules, such a proteins and small molecules such as amino acids both in-vitro and in-vivo, particularly in the non-invasive measurement of molecules in-vivo. Examples of such molecules include:

(i) Amino acids and related compounds such as taurine, glutamine, N-acetyl-L-asparate (NAA), homocysteine
(ii) Lipids such as phospholipids e.g. phosphatidylcholine and related intermediates such phosphocholine;
(iii) Lipid binding proteins such as lipoprotein A, HDL, LDL;
(iv) Peptides/Proteins such as PARK 7, Nucleoside Diphosphate Kinase A (NDKA), amyloid beta peptide, Tau (e.g. hyperphosphorylated Tau), CD68, CD64, carcino-embryonic antigen (CEA), tumor-associated glycoprotein 72 (Tag72), folate receptor-α, Alpha actin, Toll-like receptors (TLRs) Creatine, Creatinine, amyloid precursor protein (APP), troponin, C-reactive protein, Fibrinogen, B-type natriuretic peptide (BNP)
(v) Enzymes such as phospholipases such as phosopholipase $A_2$, β-secretase, γ-secretase, succinate dehydrogenase (SDH), fimarate hydratase (FH), neprilysin (NEP), endothelin-converting enzyme (ECE), insulysin (IDE), angiotensin-converting enzyme (ACE) and matrix metalloproteinases 1-9 (MMP 1-9), Creatine kinase (CK), creatine kinase isoenzyme MB (CKMB)
(vi) Cytokines such as IL(1-6) and TNFα;
(vii) Other small molecule metabolites such as lactate, glucose, acetyladehyde hydrate, acetate, choline, inositol
   Note MMP 1-9 refers to matrix metalloproteinase 1, matrix metalloproteinase 2 and matrix metalloproteinase 3 etc up to and including matrix metalloproteinase 9.
   Note IL(1-6) refers to interleukin 1, interleukin 2, interleukin 3 etc up to and including interleukin 6.
For the avoidance of doubt an enzyme is a protein.

Such molecules can be used in the detection and/or diagnosis of a number of disease conditions, for example:
Cardiac disease: C-reactive protein, Creatine kinase (CK), creatine kinase isoenzyme MB (CKMB), troponin;
Stroke: PARK 7, Nucleoside Diphosphate Kinase A (NDKA), phospholipases such as phosopholipase $A_2$, homocysteine;
Atherosclerosis: CD68, phosopholipase $A_2$, Lipopronin, endothelin-converting enzyme (ECE);
Alzheimer's disease/vascular dementia: amyloid precursor protein (APP), β-secretase, γ-secretase, amyloid beta peptide, Tau (e.g. hyperphosphorylated Tau);
Cancer: succinate dehydrogenase (SDH), fumarate hydratase (FH), carcino-embryonic antigen (CEA), tumor-associated glycoprotein 72 (Tag72), folate receptor-α.

In methods of the invention, detection and/or diagnosis of a disease condition may be facilitated by the measurement of one molecules or more than one molecule.

In methods of the invention measurement of molecules in the millimolar and micromolar range is envisaged. In addition, measurement of molecules in the picomolar range is envisaged.

In one embodiment the rare earth metal is selected from: $Ce^{4+,3+}$, $Yb^{3+}$, $Eu^{3+}$, $Sm^{3+}$, $Tm^{3+}$, $Tb^{3+}$, $Er^{3+}$, $Ho^{3+}$, $Dy^{3+}$, $Pr^{3+}$ and $Nd^{3+}$. In a further embodiment the rare earth metal is selected from: cerium, europium and ytterbium.

In a further embodiment of the invention, there is provided a method for the non-invasive measurement of a metabolite in an animal which comprises:
(i) administering a rare-earth tagged metal marker to said animal;
(ii) optically coupling a body part of said animal with a light source and a light detector,
(iii) detecting a rare earth metal-conjugated marker to generate an optical signal; and
(iv) processing said optical signal to calculate a level or change in level of the metabolite;
and optionally: correlating the level or change in level of said metabolite to a disease condition.

Administration of a rare earth conjugated marker may be by any suitable route for example, orally or by injection.

In a further embodiment of the invention there is provided a method for the non-invasive measurement of a metabolite in an animal which comprises:
(i) optically coupling a body part of said animal with a light source and a light detector;
(ii) detecting a rare earth metal-conjugated marker to generate an optical signal; and
(iii) processing said optical signal to calculate a level or change in level of the metabolite;
and optionally:
(iv) correlating the level or change in level of said metabolite to a disease condition.

Non-invasive analysis of metabolites using rare-earth tagged molecules can be used to direct therapy.

Therefore, according to a further aspect of the invention there is provided a method of treating a disease comprising using a rare earth metal-conjugated marker to detect the level or change in level of a metabolite and using the level or change in level of the metabolite to direct therapy.

According to a further aspect of the invention there is provided a method of directing surgery comprising using a rare earth metal-conjugated marker to detect the level or change in level of a metabolite and using the level or change in level of the metabolite to direct surgery.

According to a further aspect of the invention there is provided a method of directing surgery comprising using a rare earth metal-conjugated marker to localise a pathological area of an animal and using said localisation to direct the pint of surgical intervention in the animal.

A pathological areas comprises areas where tissue may be removed to aid in treatment of a patient. Such areas include cancerous tissue and atherosclerotic tissue.

According to a further method of the invention there is provided a method of treating a disease condition in an animal comprising:
(i) administering a rare earth metal-conjugated marker to said animal;
(ii) optically coupling a body part of said animal with a light source and a light detector;
(iii) detecting a rare earth metal-conjugated marker to generate an optical signal;
(iv) processing said optical signal to
   a. calculate a level or change in level of the metabolite; and or
   b. calculate the position of the rare earth meal conjugated marker,
(v) using said position, level or change in level to aid in treatment of said disease condition.

According to a further method of the invention there is provided a method of treating a disease condition in an animal comprising:
(i) optically coupling a body part of said animal with a light source and a light detector,
(ii) detecting a rare earth metal-conjugated marker to generate an optical signal;
(iii) processing said optical signal to
   a. calculate a level or change in level of the metabolite; and or
   b. calculate the position of the rare earth meal conjugated marker;
(iv) using said position, level or change in level to aid in treatment of said disease condition.

Treatment of a disease condition comprises an activity directed by a medical practitioner, such as a doctor or nurse, for example, administration of a pharmacologically active substance, reducing or increasing the dose of a pharmacologically active substance, ceasing administration of a pharmacologically active substance or hospitalization, defining appropriate surgical intervention or defining the site of surgical intervention.

For the avoidance of doubt a pharmacologically active substance may comprise one or more pharmacologically active substances.

In one embodiment of the present invention a photoluminescence intensity ratio (PLIR) imaging technique may be used to calculate the level or a change in level of the metabolite. In a preferred embodiment the PLIR imaging technique may be used to detect biomarkers indicative of disease in a given medium, more preferably to detect the amounts of biomarkers indicative of disease in a given medium.

In a non-limiting example PLIR may be used to detect the one or more biomarker for atherosclerosis. The or each biomarker may be any suitable biomarker indicative of atherosclerosis. For example, in one embodiment the or each biomarker may be phospholipids and/or lactic acids, suitably, lactic acid. The or each biomarker may be conjugated with any suitable rare earth metal. Preferably, the rare earth metal is selected from one or more of $Ce^{4+,3+}$, $Yb^{3+}$, $Eu^{3+}$, $Sm^{3+}$, $Tm^{3+}$, $Tb^{3+}$, $Er^{3+}$, $Ho^{3+}$, $Dy^{3+}$, $Pr^{3+}$ or $Nd^{3+}$, particularly preferred being $Eu^{3+}$.

The photoluminescence intensity ratio (PLIR) for $Eu^{3+}$-conjugated lactic acid is defined as $I_{616}/I_{591}$, i.e. the ratio of the intensity of the fluorescence emission peak at 616 nm to the intensity of the fluorescence emission peak at 591 nm. Emission at 616 nm gives rise to red light and emission at 591 nm gives rise to yellow light. An increase in the fluorescence emission at 616 nm will lead to an increase in the PLIR and resulting images will appear more red in colour.

At lower lactic acid concentrations the main fluorescence peak emission of $Eu^{3+}$ conjugated to lactic acid is at 616 nm. Therefore at low lactic acid concentrations the PLIR>1. At higher lactic acid concentrations the main fluorescence peak emission is at 593 nm. Therefore at high lactic acid concentrations the PLIR<1. A plot of PLIR versus lactic acid concentration, at a given $Eu^{3+}$ concentration, can be used as a calibration for the determination of the concentration of lactic acid based on the measured PLIR. The lactic acid concentration may be given in any suitable form. Preferably the lactic acid concentration is given as a molar fraction. Under either high lactic acid concentrations or low lactic acid concentrations, an increase in lactic acid concentration will lead to an increase in PLIR and the resulting images will appear more red in colour.

For the avoidance of doubt the above mentioned method is not limited to the detection of $Eu^{3+}$ conjugated lactic acid. It will be clear to a person skilled in the art that the emission wavelengths used to calculate the PLIR will change depending on the rare earth metal and/or the metabolite.

According to yet a further aspect of the present invention there is provided a method of treating a disease condition in an animal comprising:
(i) administering $Eu^{3+}$ or a source thereof to said animal;
(ii) optically coupling a body part of said animal with a light source and a light detector;
(iii) detecting $Eu^{3+}$-conjugated lactic acid to generate an optical signal;
(iv) processing said optical signal to
 a calculate a level or change in level of $Eu^{3+}$-conjugated lactic acid; and or
 b calculate the position of $Eu^{3+}$-conjugated lactic acid;
(v) using said position, level or change in level of lactic acid to aid in treatment of atherosclerosis
wherein the level or change in level of $Eu^{3+}$-conjugated lactic acid in step (iv) is determined using the photoluminescence intensity ratio ($=I_{616}/I_{591}$).

Contrary to expectation we found that rare earth tagged molecules were not toxic to cells. In fact we observed that the rare earth tagged molecules were cytoprotective for cells. Thus, according to further aspect of the invention there is provided the use of a rare earth tagged markers as a cytoprotective.

Rare earth tagged markers suitable for use in non-invasive measurements of metabolites in-vivo represent a further aspect of the invention. Therefore, according to a further aspect of the invention there is provided a rare-earth tagged marker compound.

According to a further aspect of the invention there is provided a compound comprising a rare earth metal conjugated to a compound selected from one of the following groups:
(i) small molecule metabolites such as amino acids, lactic acid, glucose, taurine, glutamine,
(ii) lipids, such as phospholipids
(iii) peptides; and
(iv) proteins.

Rare earth elements are coupled compounds depending on the chemistry of the particular molecule and the number of functional groups (for example, carboxy and phosphate groups) available, for example
(i) in molecules comprising a carboxylic acid rare earth metals can interact with the acid group, for example with the formation of a salt;
(ii) in molecules with an amino group ($-NH_2$) group rare earth metals can interact with the amino group;
(iii) in molecules with a phosphate group rare earth metals can interact with the phosphate group;
(iv) in molecules with a hydroxyl group rare earth metals can interact with the hydroxyl group;
(v) in molecules with a thiol ($-SH$) group rare earth metals can interact with the thiol group.

In some molecules only one functional group would be available for interaction, in other molecules a number of functional groups would be available for interaction. For example, in a peptide or protein a number of rare earth metal ions would be expected to be bound to the peptide or protein depending on the number and nature of the amino acid side chains in the peptide or protein.

In a further embodiment of the invention there is provided a rare earth metal conjugated molecule selected from:
(i) a carboxylic acid such as a lactate chelate of a rare earth metal;
(ii) a phosphate chelate of a rate earth metal, for example a chelate comprising a phospholipid such as phosphatidylcholine;
(iii) an amino acid conjugated to a rare earth metal, such an amino acid may be conjugated via one or more of the carboxy group, the amino group and the side chain.
(iv) A protein conjugated to a rare earth metal, such as a phospholipase conjugated to a rare earth metal, e.g. phospholipase $A_2$.

In a further embodiment of the invention there is provided a rare earth metal conjugated molecule selected from:
(i) Lactate conjugated to a rare earth metal, for example conjugated to cerium, europium or ytterbium;
(ii) Phospholipase $A_2$ conjugated to a rare earth metal, for example conjugated to cerium, europium or ytterbium;
(iii) Phosphatidycholine conjugated to a rare earth metal, for example conjugated to cerium, europium or ytterbium;
(iv) Phosphocholine conjugated to a rare earth metal, for example conjugated to cerium, europium or ytterbium;
(v) Lecithin conjugated to a rare earth metal, for example conjugated to cerium, europium or ytterbium;

In a further embodiment of the invention, there is provided a method of preparing a rare-earth metal conjugated compound of the invention. In general rare earth metal conjugated compounds are prepared by mixing a salt of a rare earth metal (for example, a nitrate salt, an acetate salt or a chloride salt) with said compound in a suitable solvent such as water or a suitable buffer followed by separation of the rare earth metal conjugated compound from the free rare earth metal ions.

Therefore, in one embodiment of the invention there is provided a method of preparing a rare-earth metal conjugated compound of the invention comprising:
(a) mixing a rare earth metal salt with a compound in the presence of a suitable solvent; such that rare earth metal ions associate with the compound, and
(b) separating the rare earth metal conjugated compound from the unreacted rare earth metal ions.

In a further embodiment of the invention there is provided a method of preparing a rare-earth metal conjugated compound of the invention comprising:
(a) dissolving a rare earth metal in water or a suitable buffer to form a solution of rare earth metal ions;
(b) dissolving a compound in water or a suitable buffer,
(c) mixing the solution of rare earth metal ions with the compound solution such that the rare earth metal ions associate with the compound; and
(d) separating the rare earth metal conjugated compound from the unreacted rare earth metal ions.

Rare earth tagged markers can be measured by a number of spectroscopic techniques including Raman spectroscopy, Laser spectroscopy, Fourier transform infrared spectroscopy.

The imaging system may utilize single or plurality, monochromatic or multi-wavelength (e.g. white light) light(s) for imaging. Images may be detected by a 2-D sensor, or camera for real-time targeting and feedback on a surface, or subsurface of tissue.

Raman spectroscopy has been used for many years to probe the molecular structure and biochemistry of various biological tissues [Motz et al, (2005) J. Biomed. Opt 10:1-7.]. The technique relies on inelastic scattering, or Raman scattering, of UV, visible or near-infrared light to provide information about the concentration of and the structure, bonding and local environment in organic and inorganic species by recording a spectrum of characteristic peaks due to their molecular vibrations. Raman scattering can also be excited by X-ray radiation that is commonly available from synchrotron sources [de Groot (2001) Chemical Reviews 101: 1779-1808]. Typically, the vibrational spectrum is excited by illuminating a sample with monochromatic light that is usually provided by a laser. The incident probe laser light beam is focused on or inside the sample using a lens, or alternatively directed to the sample using an optical fibre. The light beam interacts with the sample, producing vibrational excitations that result in the incident laser wavelength and energy being shifted away from their initial values by small amounts corresponding to the vibrational energies of the sample. The result is a scattering of radiation from the excited region within the sample containing the spectrum of inelastically or Raman scattered wavelengths that correspond to the vibrational spectrum. Further details of the physical nature of the Raman scattering process and its application to understanding or monitoring the vibrational modes and molecular structures in samples and materials with applications including molecular biochemistry, medicine and biology are discussed and described in several standard textbooks including (i) Tobin, M. G. 1971. Laser Raman Spectroscopy. Wiley-Interscience, New York.
(ii) Hendra, P. J., C. Jones, and G. Warnes. 1991. Fourier Transform Raman Spectroscopy. Ellis Harwood, N.Y.; and
(iii) Long, D. A. 2002. The Raman Effect. John Wiley and Sons, New York.

Laser spectroscopy refers to a branch of spectroscopy in which a laser is used as an intense, monochromatic light source; using tunable lasers and other types of coherent emission sources, such as optical parametric oscillators. This allows selective excitation of atomic or molecular species. increasing the resolution and sensitivity of conventional spectroscopic techniques. For more information the reader is referred to:
(i) W. Demtröder, Laser Spectroscopy, 3rd Edition. (Springer, 2003).

Spectroscopic methods of the invention utilise wavelengths suitable for excitation and detection of rare earth metal-conjugated markers, such as in the range about 600 nm to about 2100 nm. In particular, wavelengths which utilise the optical transparency of mammalian skin (about 600 to about 1400 nm) window. In further embodiments:
(i) Excitation in the range about 600 nm to about 2100 nm.
(ii) Measurement in the range about 600 nm to about 2100 nm.
(iii) Excitation in the range of about 600 nm to 1300 nm;
(iv) Excitation in the range about 1500 nm to about 2000 nm
(v) Excitation at about 514 nm;
(vi) Excitation at about 980 nm;
(vii) Excitation at about 250 nm and/or excitation at about 295 nm.
(viii) Excitation at about 300 nm and/or excitation at about 392 nm
(ix) Measurement in the range about 800 nm to about 1400 nm;
(x) Measurement in the range of about 500 nm to about 700 nm;
(xi) Excitation in the range about 800 nm to about 1400 nm and measurement in the range about 800 nm to about 1400 nm;
(xii) Excitation in the range about 930 nm to about 980 nm and measurement in the range about 970 nm to about 1200 nm;
(xiii) Excitation in the range of 780-1600 and measurement in the range of 1500-2500 nm.

In general energies up to about 500 mW can be used with methods of the invention. Although when a focussed laser are used energies less than 50 mW are usually used. For example in the range about 1 mW to about 50 mW, such as about 1 mW to about 25 mW, about 1 mW to about 10 mW, about 10 mW to about 20 mW.

The term 'about' when used in this specification refers to a tolerance of ±10%, of the stated value, i.e. about 50% encompasses any value in the range 45% to 55%, In further embodiments 'about' refers to a tolerance of ±5%, ±2%, ±1%, ±0.5%, ±0.2% or 0.1% of the stated value.

The term 'animal' refers to any biological organism, for example, a mammal, such as humans, non-human primates such as monkeys, dogs, cats, horses, sheep, goats, cows, rabbits, pigs and rodents, for example mice and rats. In one embodiment the animal is a human. In a further embodiment the animal is a mouse or a rat.

The term 'cytoprotective' refers to a chemical compounds which protects cells against harmful agents. For example, the protection of cells against free radicals.

The term 'laser-based analysis' refers to any technique which comprises applying a laser to a biological material and measuring the energy absorbed/scattered or energy emitted from the material, for example inputting energy at a first wavelength and measuring energy emitted at a second wavelength or across a range of wavelengths. Examples of laser based analysis include laser spectroscopy and Raman spectroscopy.

The term 'marker' refers to any compound which facilitates measurement of a metabolite, for example a metabolite conjugated to a rare earth metal.

The term 'metabolite' refers to any molecule within the animal body involved in the biochemical processes of said animal, for example small molecules with a molecular weight of less than 500 Daltons such as glucose and lactate, peptides, lipids and proteins.

The term 'rare earth element' or 'rare earth metal' refers to a set of seventeen chemical elements in the periodic table, specifically the fifteen lanthanides plus scandium and yttrium. The rare earth elements comprise: Cerium (Ce), Dysprosium (Dy), Erbium (Er), Europium (Eu), Gadolinium (Gd), Holmium (Ho), Neodymium (Nd), Praseodymium (Pr), Samarium (Sm), Terbium (Tb), Thulium (Tm) and Ytterbium (Yb).

The term 'small molecule metabolite' refers to a metabolite with a molecular weight of less than 500 Daltons.

The term 'mole fraction' refers to the ratio of the number of moles of a substance in a mixture or solution to the total number of moles of all the components in the mixture or solution.

The term 'photoluminescence intensity ratio (PLIR)' refers to the ratio of the intensity of two different fluorescence emission peaks at a given rare earth metal concentration.

The invention will now be illustrated with the following non-limiting examples with reference to the following figures.

FIG. 1 shows the emission spectrum of $Eu^{3+}$ doped lactic acid in two different concentration ranges:
  (a) the fluorescence emission spectra of 0.5M europium nitrate alone and in the presence of a variation of concentrations of lactic acid when excited at 395 nm. The mole fraction of lactic acid is of the order of $10^{-6}$
  (b) the fluorescence emission spectra of 0.5M europium nitrate in the presence of a variation of concentrations of lactic acid when excited at 395 nm. The mole fraction of lactic acid is of the order of $10^{-3}$ FIG. 2 These graphs represent the cell viability of neuroblastoma cells using the MTT assay (Experiment 2) in the presence of a variation of concentrations of ytterbium nitrate for 24 hours (a) and 5 days (b) compared to a control average. The concentrations are plotted on the x-axis where the control population were not administered any ytterbium nitrate. The bar represents the Mean for the viability compared to the control average, with the Standard Error of the Mean also shown above the bar.
  For (a) n=32 and for (b) n=16. All groups were compared with the Mean at a level of significance $p<0.05$.
  **=$p<0.01$.

Figure 6:
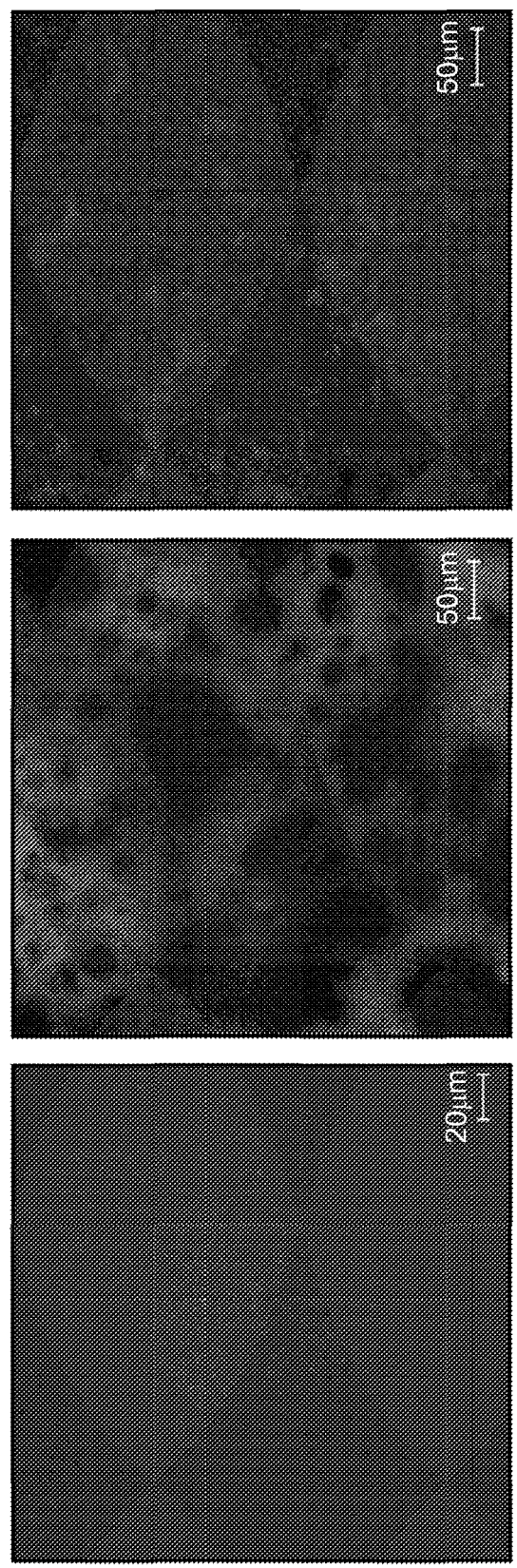

FIG. 6. shows confocal laser scanning microscope images of a phospholipid control (a), $Eu^{3+}$ conjugated phospholipid (b) and $Eu^{3+}$ conjugated lactic acid (c). Images were taken in the wavelength range 570 to 650 nm with a diode laser at 405 nm. The image of phospholipids conjugated with $Eu^{3+}$ is predominantly yellow-orange and that of $Eu^{3+}$ conjugated lactic acid is predominantly reddish in colour.

FIG. 7; shows the photoluminescence intensity ratiometric (PLIR=$I_{616}/I_{591}$) determination principle.
  (a) Photoluminescence intensity ratio corresponding to PLIR>1 for mole fraction of lactic acid in solution with lactic acid in lower concentration (left Y-axis) and for mole fraction of europium nitrate in solution (right Y-axis).
  (b) Photoluminescence intensity ratio corresponding to PLIR<1 case for mole fraction of lactic acid in solution with lactic acid in higher concentration (left Y-axis) and for mole fraction of europium nitrate in solution (right Y-axis).

Figure 8:
Figure 8:
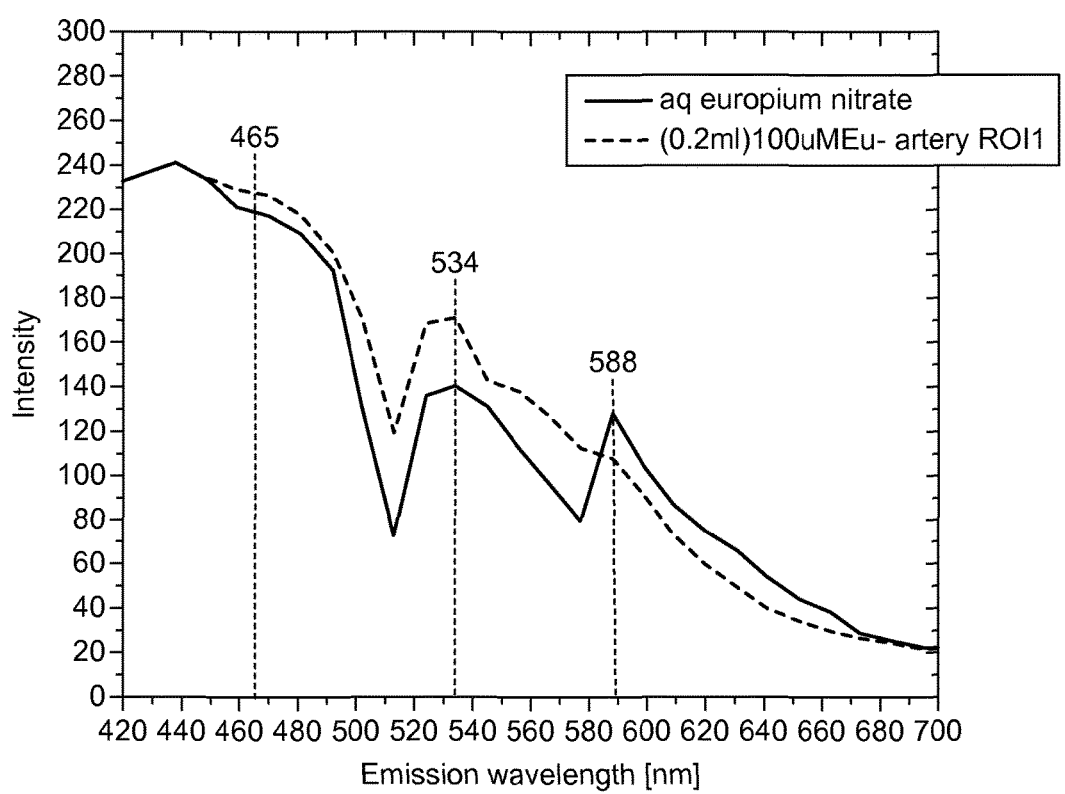
Figure 9:
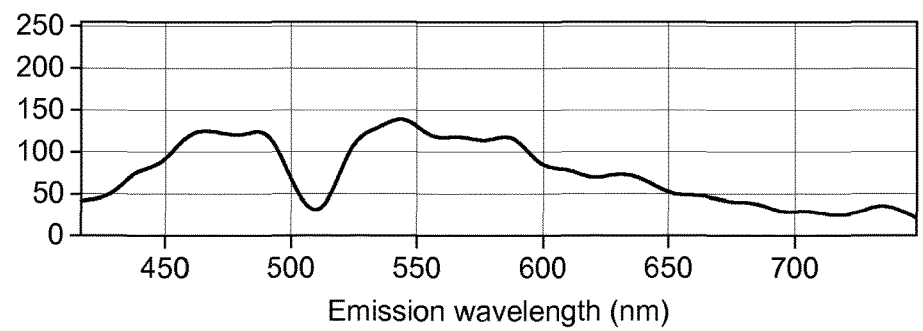
Figure 9:
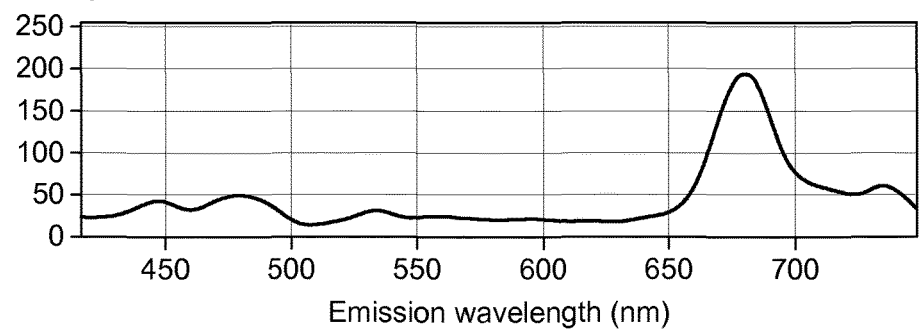
Figure 9:
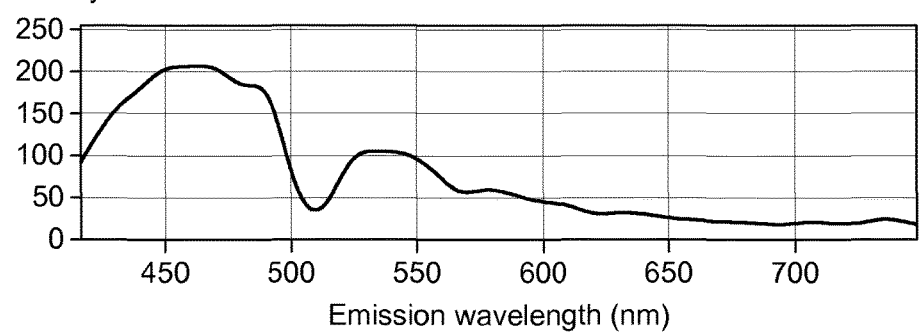
Figure 9:
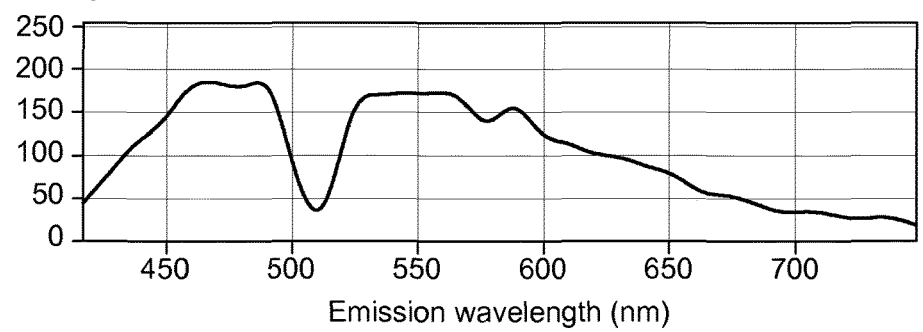
Figure 9:
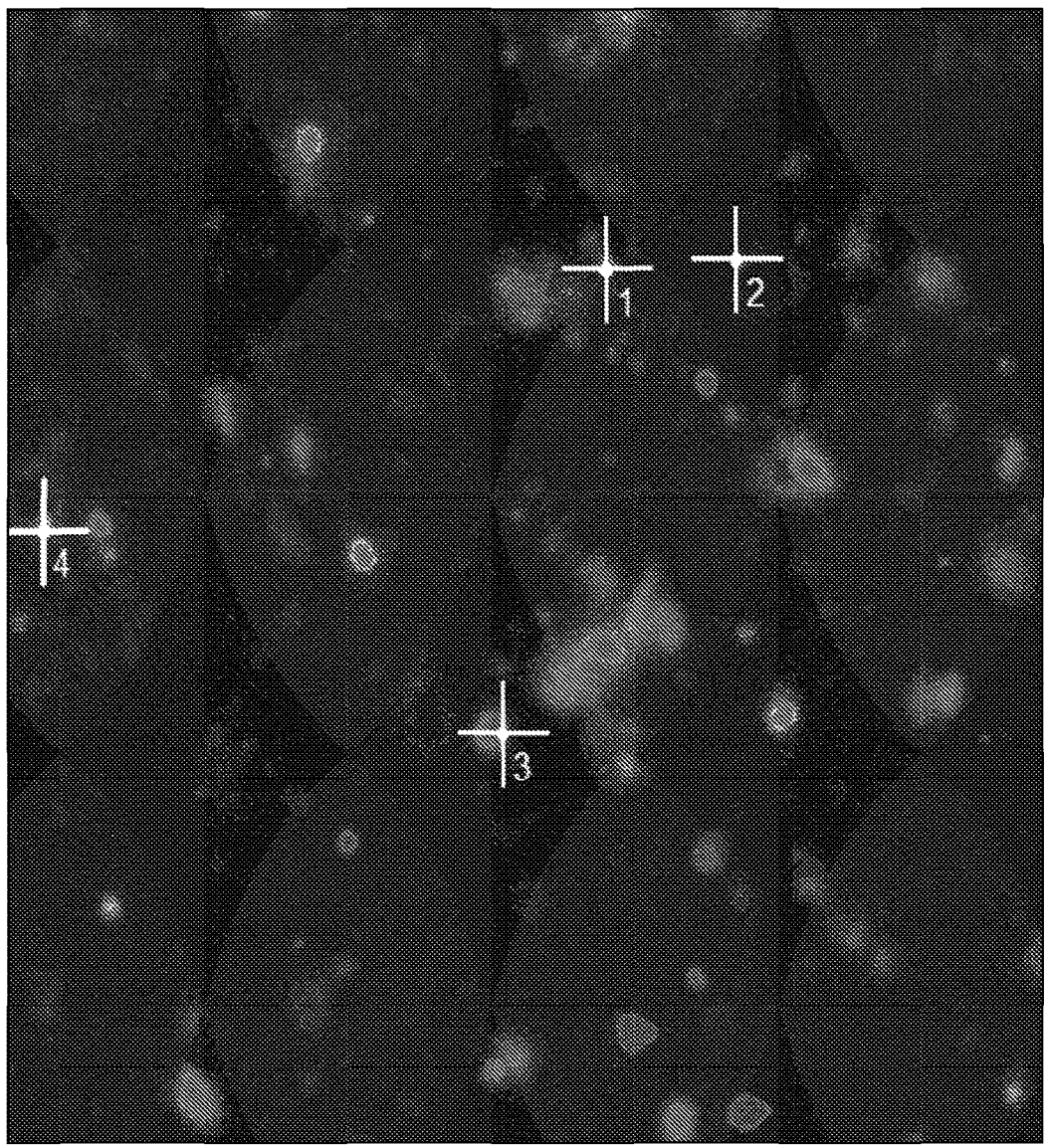

FIG. 8 shows (a) confocal image of (0.2 ml) 100 μM europium nitrate with mouse artery when excited with diode laser at 405 nm. (b) Fluorescence emission spectra for 100 μM aq europium nitrate with mouse artery FIG. 9 shows Cerebellum sections following IP administration of europium nitrate.

Figure 10A:
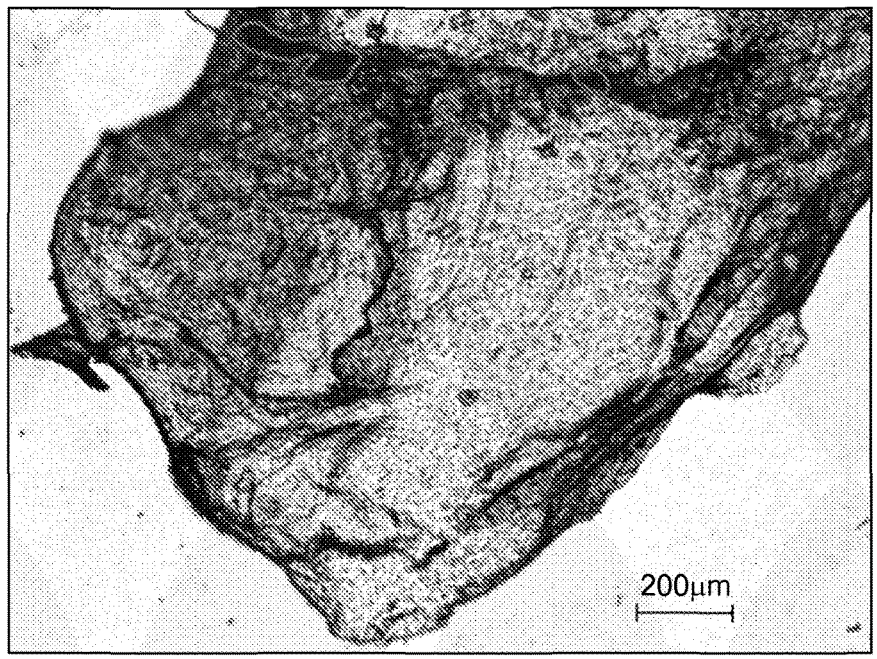

FIG. 10 shows a mouse carotid artery treated with 100 μM europium as seen under:
  (a) bright field microscopy; and
  (b) under fluorescence microscopy using a DAPI filter (which allows emission in the range 470 nm-500 nm)
  The fluorescent areas (white in the black and white image) in (b) are the areas where europium has conjugated with the lipid regions of the artery.

Figure 11A:
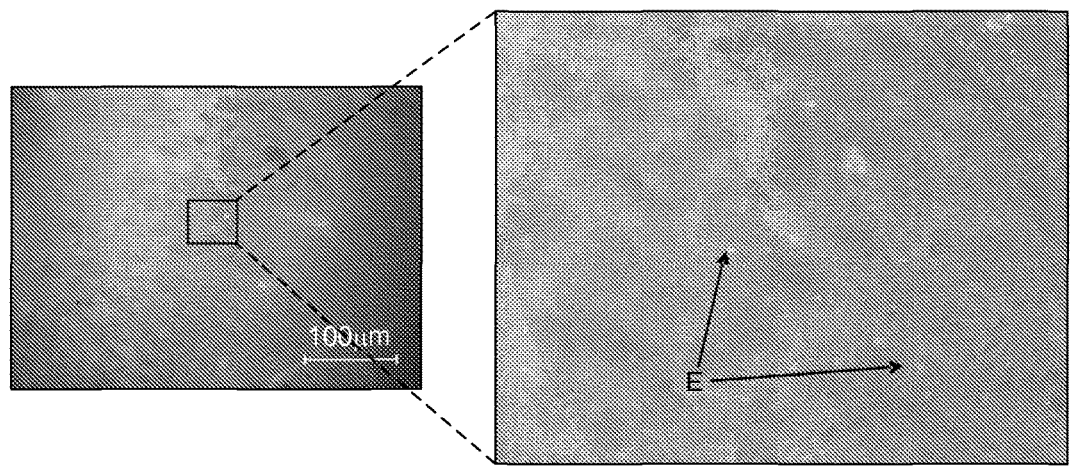
Figure 11B:
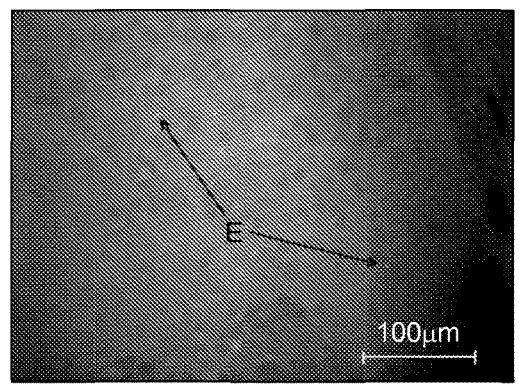
Figure 11C:
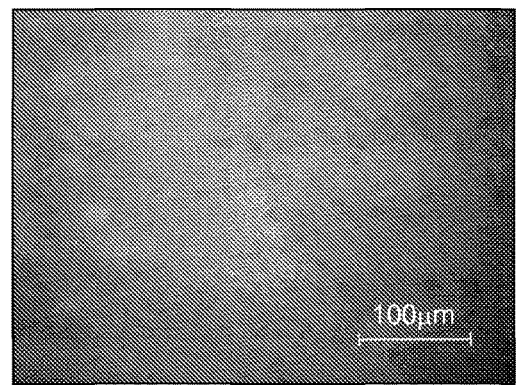

FIG. 11 shows confocal laser scanning microscope images of mouse brain tissue exposed to different concentrations of europium nitrate at 20× magnification. E represents the presence of europium ions.
  (a) 0.1 μM europium nitrate (also showing 6× magnification of image)
  (b) 1 mM europium nitrate
  (c) control (no europium nitrate)

ABBREVIATIONS USED

DAPI 4',6-diamidino-2-phenylindole
MTT 3-(4,5-Dimethylthiazol-2-yl)-2,5-Diphenyltetrazolium Bromide
PBS Phosphate-buffered saline
RE Rare earth metal
UV ultraviolet
VIS visible Example 1—Preparation of Rare-Earth Metal Tagged Molecules For conjugation studies using ytterbium nitrate $Yb(NO_3)_3$ this was first dissolved in distilled water (0.01M) which provided a pH of 5.66, outside of the desirable range of 6.5 to 7.5 which is close to physiological ranges. Titration between ytterbium nitrate solution and NaOH was unsuccessfully performed in an attempt to neutralize the acidity.

$Yb(NO_3)_3$ solutions were prepared in phosphate buffered saline (PBS, pH7.2) varying from 0.01M to 1M without any significant change from the initial pH of the buffer solution. When analysed for UV/VIS, the wavelength of maximum absorption of $Yb(NO_3)_3$ dissolved in 7.2 pH buffer was consistent for all the concentrations analysed, with 7 concentrations having a maximum peak at 970 nm and the remaining 3 at 971 nm. It was clear from the initial pH trial that $Yb(NO_3)_3$ is a hydrogen donor, which is why as its concentration increases in water, the pH of its solutions decreases.

The results from the final trial suggest that $Yb(NO_3)_3$ is adequately buffered in the 7.2 pH buffer to remain within the target range (6.5-7.5 pH) for the highest concentration of ytterbium solution that is intended to be used (1M). For conjugation with phospholipid (L-α-Lecithin, Egg Yolk (from Merck Chemicals Ltd)), 100 µM solutions were prepared either in distilled deionised water or in a cell culture medium of supplemented Ham's F12 medium and Eagle's minimal essential medium as, described as SH, by Webster et al. (2004, Brain Res Mol Brain Res, 130: 161-169). to maintain the physiological environment of the cells and added to 10 ml Yb(NO3)3 solution prepared in PBS (7.2 pH). After 24 hr 1 µg of 8.4% phospholipase A2 powder from bovine pancreas (Sigma) was manually mixed into Yb(NO3)3 and phospholipid solutions after 10 minutes of thawing from a frozen state at room temperature. This mixing occurred within minutes of the analysis to prevent any adaptation, including denaturing, of the enzyme's molecular structure prior to use.

Figure 1A:
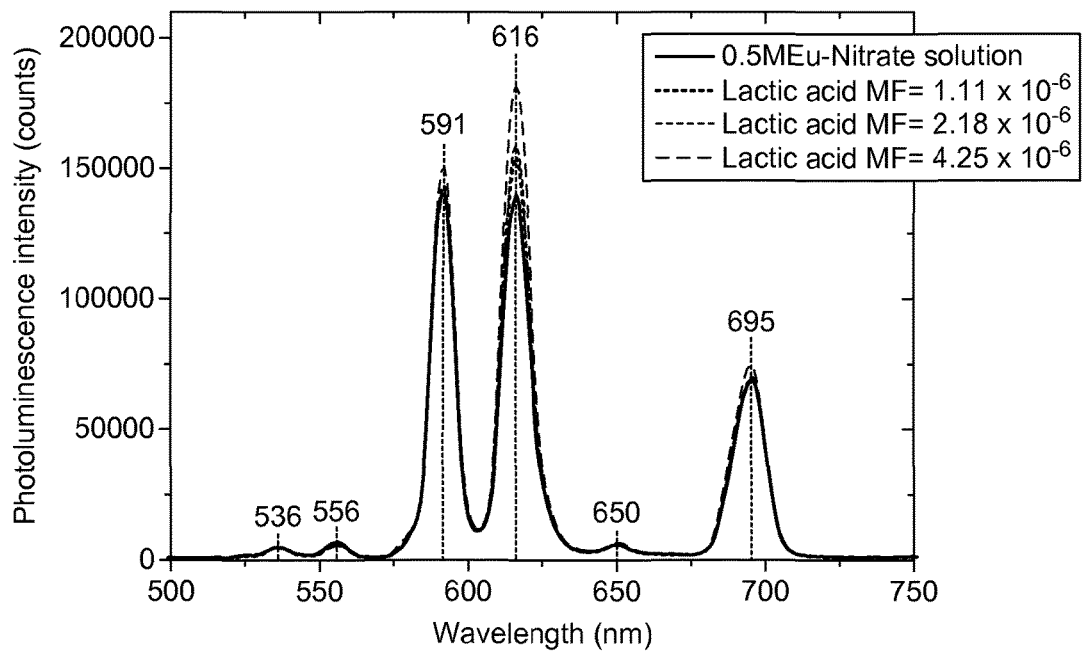
Figure 1B:
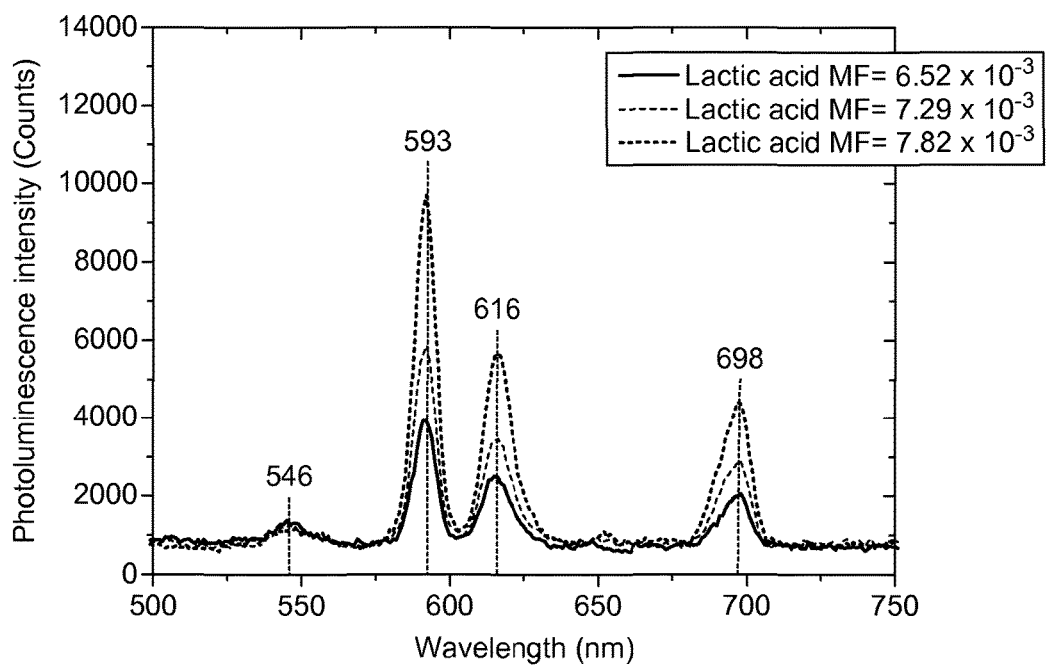

Europium was also couple to lactate. Measurements were taken and analysed at two different lactic acid concentration ranges. FIG. 1(a) shows the Fluorescence emission spectra of 0.5M europium nitrate alone and when coupled with lactic acid with lactic acid in lower concentration when excited at 395 nm. FIG. 1(b) shows the Fluorescence emission spectra of 0.5M europium nitrate alone and when coupled with lactic acid where the lactic acid is in higher concentration when excited at 395 nm. The photoluminescence intensity ratio (PLIR), defined by the ratio of the fluorescence intensity at 616 nm to the fluorescence intensity at 591 nm ($I_{616}/I_{591}$) and may represent the chemical environment of the $Eu^{3+}$ ion. As shown in FIGS. 1(a) and 1(b), the PLIR reverses when the mole fraction of lactic acid is very high compared to when the mole fraction is low, such that the PLIR>1 at low lactic acid concentrations and the PLIR<1 at high lactic acid concentrations.

Figure 7A:
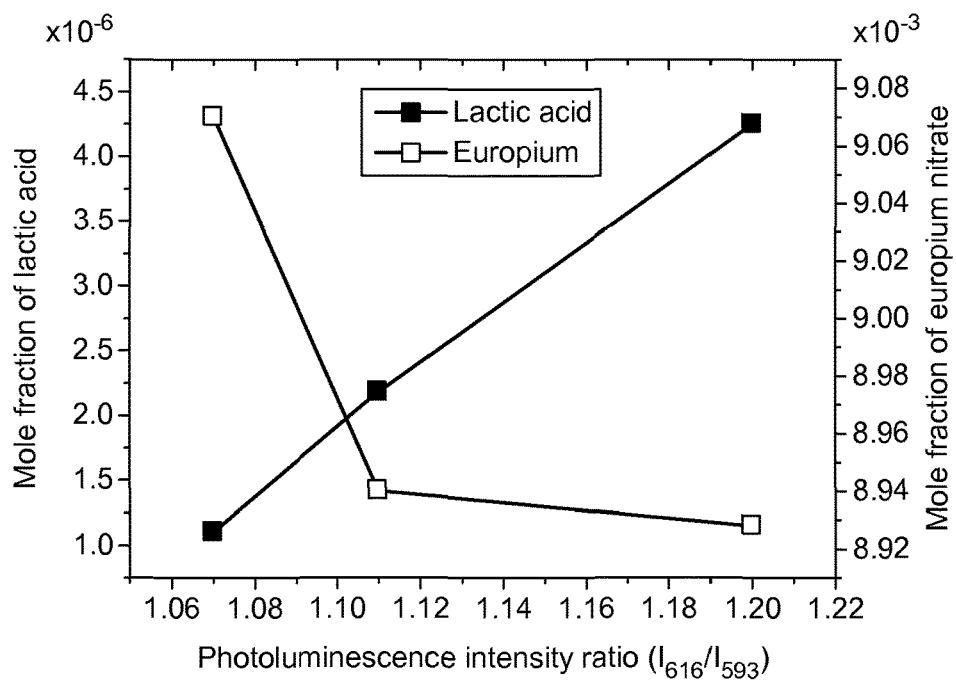
Figure 7B:
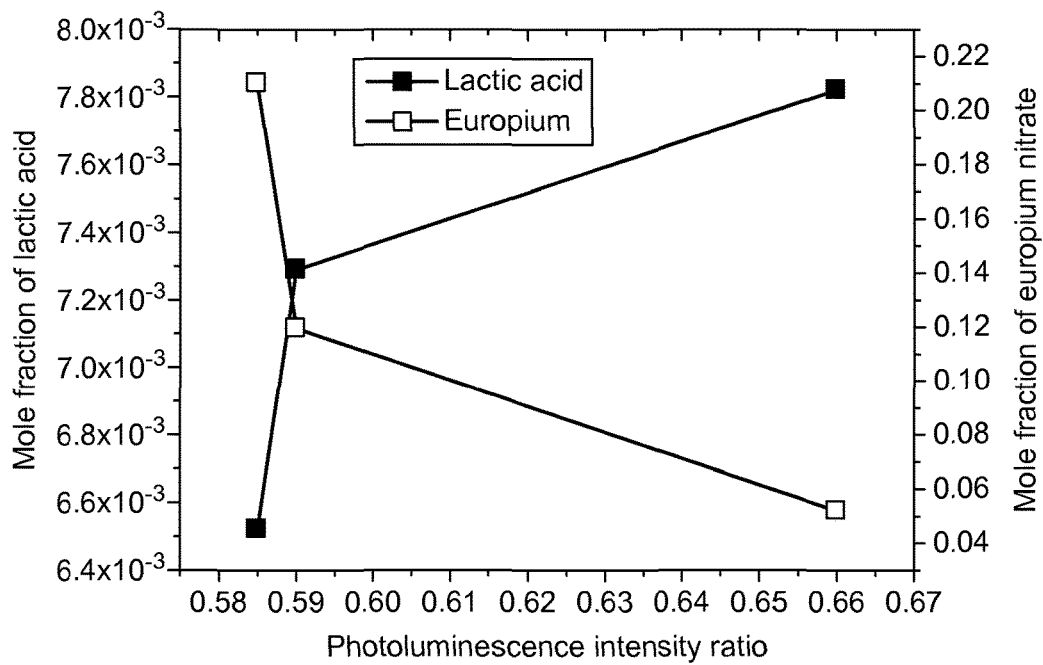

FIG. 1(a) shows that the main peak emission of $Eu^{3+}$ conjugated-lactic acid is at 616 nm when the concentration of lactic acid expressed in mole fraction is less than about $5 \times 10^{-6}$. Therefore, at low concentrations of lactic acid the PLIR is greater than 1, as plotted in FIG. 7(a). FIG. 7(a) also shows the corresponding PLIR variation with the europium nitrate mole fraction which is around $9 \times 10^{-3}$. The plot shown in FIG. 7(a) can therefore be used for calibration of the amount of lactic acid based on the measured PLIR under these conditions. When the fluorescence image is recorded under these conditions the image will be predominantly reddish as shown in FIG. 6(c). FIG. 1(b) shows the photoluminescence intensity when the mole fraction of lactic acid is at higher concentrations and the corresponding PLIR is plotted in FIG. 7(b). As shown in FIG. 1(b) the main peak fluorescence emission of $Eu^{3+}$ conjugated-lactic acid is at 593 nm when the concentration of lactic acid expressed in mole fraction is of the order of $10^{-3}$. Therefore, at high concentrations of lactic acid the PLIR is less than 1, as plotted in FIG. 7(b). The plot shown in FIG. 7(b) can therefore be used for calibration of the amount of lactic acid based on the measured PLIR under these conditions. The image will be yellowish as shown in FIG. 6(b) and the spectrum peaks at 593 nm instead of 616 nm as shown in FIG. 1(b).

Example 2—Viability of 5SH5Y Cells in the Presence of Ytterbium Nitrate

We confirmed the cell viability of 5SH5Y cells in a variation of concentrations of ytterbium nitrate using the MTT assay. The MTT Cell Proliferation Assay is a colorimetric assay system which measures the reduction of a yellow tetrazolium component (MT) into an insoluble purple formazan product by the mitochondria of viable cells which are solubilized by the addition of a detergent. The colour can then be quantified by spectrophotometric means. For each cell type a linear relationship between cell number and absorbance is established, enabling accurate, straightforward quantification of changes in proliferation. Cells derived from a sympathetic tumour were used as they proliferate rapidly (labelled human neuroblastoma cells from the SH-SY5Y cell-line (European Collection of Cell Cultures, Porton Down, Wiltshire, UK), of passage 8 to 10). These were cultured in SH medium (see Example 1) in 500 ml tissue culture flasks under incubation at 37° C. until the confluence was deemed at least 75% under microscopic analysis. Twenty-four hours before the cells were needed for treatment, cells were cultured in 96-well plates to approximately 50% confluency or greater. Experiments were carried out when all of the cell groups showed a similar confluence when viewed under the microscope. Cells were then treated with various concentrations (1 µM, 10 µM, 1000 µM, 1000 µM and 10,000 µM) of ytterbium nitrate solutions prepared in SH medium for 24 hours and 5 days. The final volume of each well after any treatment was kept at 100 µL. 11 µL Thiazolyl Blue Tetrazolium Bromide (5 mg/mL, MTT, Sigma) made up in sterile PBS was added to each well (10% by volume) and the cells were incubated at 37° C. for 3 hours. An equal volume (111 µl per well) of solubilizing solution (24 ml propan-1-ol/isopropyl alcohol (Sigma)+1.0 ml 1 M HCl) was added to each well to lyse the cells, and the contents thoroughly mixed by pipetting. Absorbance was measured at 570 nm.

The effect on cell viability was recorded after 24 hours and also over 5 days using various concentrations of ytterbium nitrate solutions. Over a 24 hour period all concentrations of ytterbium nitrate solution had a notable effect on the viability of the cell population compared to the control. The trail involving 10,000 µM showed this level of ytterbium to be detrimental to cell survival and proliferation, whereas all the others were shown to be beneficial.

Figure 2A:
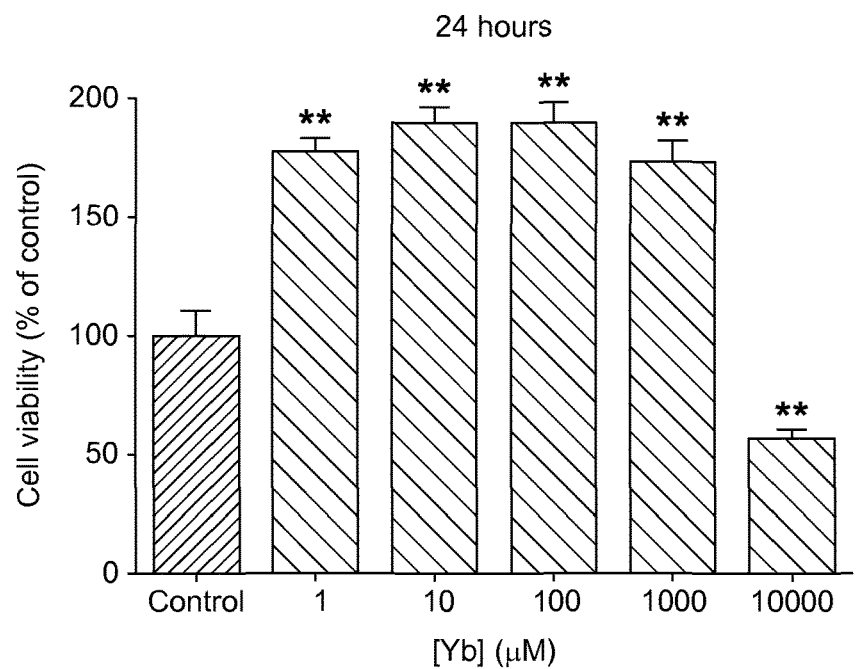
Figure 2B:
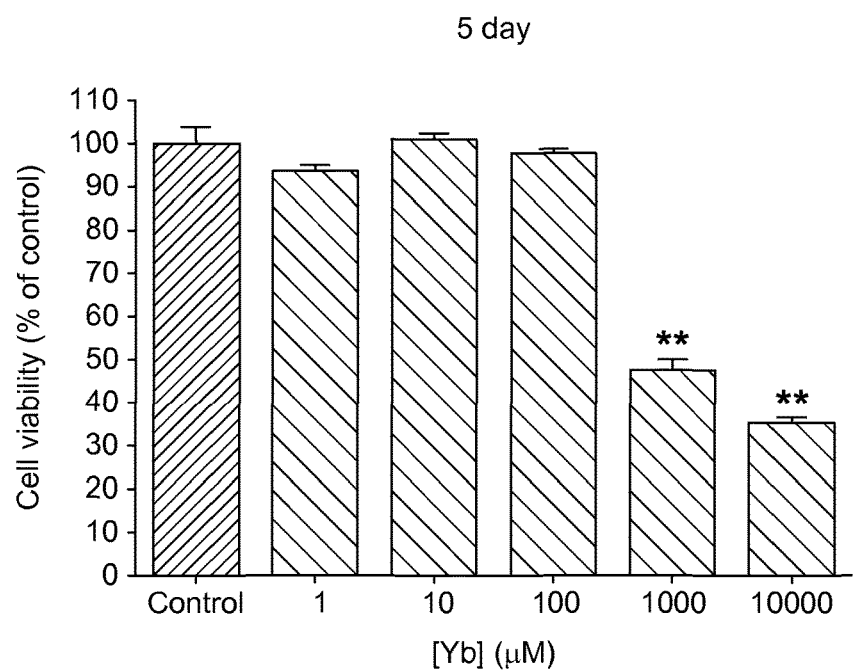

One-way ANOVA (and nonparametric) statistical test with a Dunnett post test was completed on the data, with significance defined as $p<0.05$. This test was chosen as it is able to make multiple group comparisons and was performed through the software GraphPad Prism. The cell viability results are shown in FIG. 2 (a, b). We also performed the cytotoxicity test for europium and cerium. Our results show that both lanthanides are significantly non-toxic when compared with control (untreated cells). However cytotoxic effects of both compounds were observed at 10,000 µM concentration at 5 days of treatment.

Example 3—Cytoprotective Test

Cytoprotective effect tests were performed on SH-SY5Y cells that had previously been exposed to hydrogen peroxide for 24 hours. Hydrogen peroxide ($H_2O_2$) is a strong oxidant, and its activity is based on hydroxide radical's action on DNA strand ((Jonas et al, 1989, Biochem. J., 264, 651-655.). Cells were cultured in 96-well plates to approximately 50% confluency or greater. Experiments were carried out when all of the cell groups showed a similar confluency when viewed under the microscope. To kill the cells, 500 µM of hydrogen peroxide (dissolved in SH medium) were added to cell culture 24 hours prior to additions of cerium and europium nitrate (dissolved in SH medium), and this concentration is deemed adequate to kill a considerable number of cells to measure good cytoprotective test result (Gülden et al, 2010, Free Radic Biol Med. 49:1298-305). Cell viability was measured after 24 hours exposure to cerium and europium nitrate using the MTT assay as described above.

Figure 3:
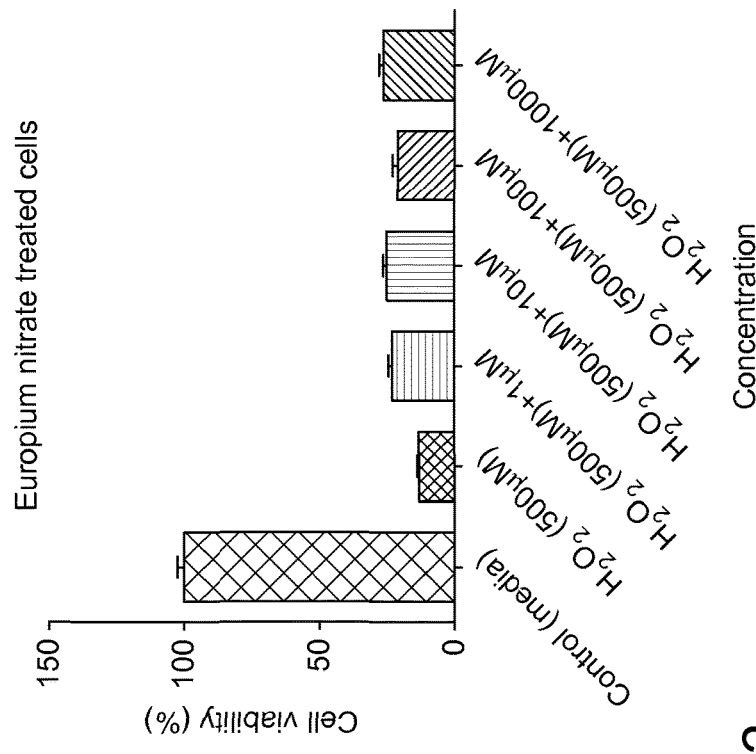
FIG. 3 shows cytoprotective test results for SH-SY5Y cells treated with cerium or europium nitrate solution for 24 hours after treatment with hydrogen peroxide for 24 hours.
Figure 3:
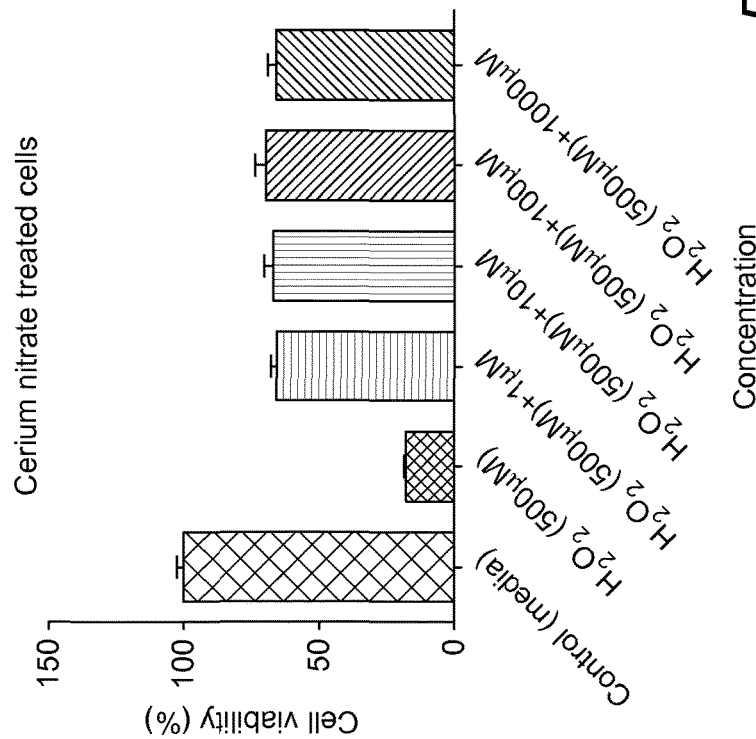

Further data interpretation and statistical analysis by using one-way ANOVA and Dunnett post-test (n=80, 95% confidence) shows that both lanthanides especially cerium significantly inhibiting hydrogen peroxide's cytotoxicity. Based on the cytoprotective test results, cerium nitrate is a more potent antioxidant-based cytoprotective agent compared to europium nitrate. The results are shown in FIG. 3.

Example 4—Confocal Laser Scanning Microscopy Results

In Vitro Study

Figure 4:
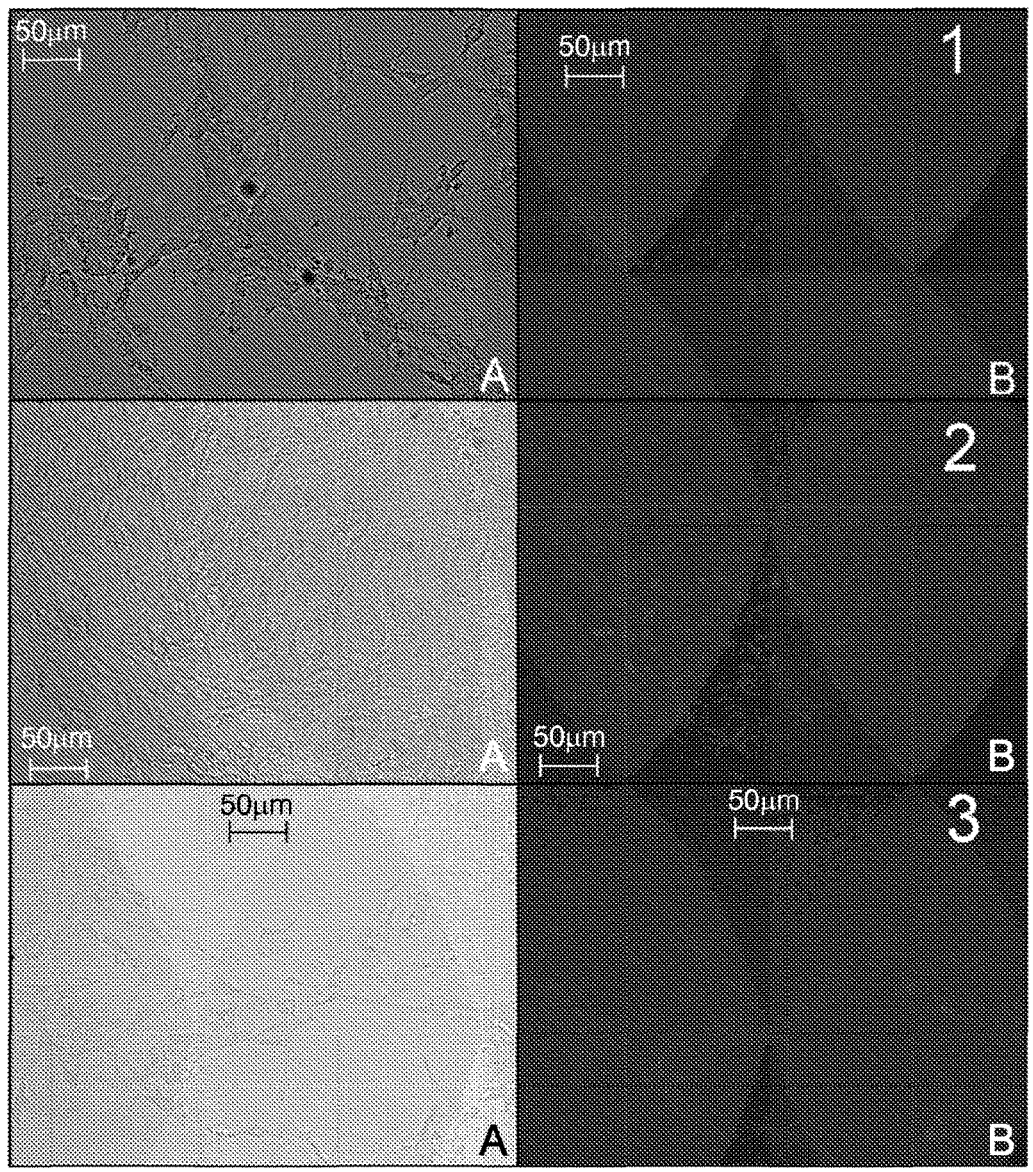
FIG. 4 shows fluorescence microscopy images of untreated SH-SY5Y cells (1), previously treated with 1000 μM cerium nitrate for 24 hours (2), and previously treated with 1000 μM europium nitrate for 24 hours (3).

For confocal laser scanning microscopy SH-SY5Y cells were grown as above, harvested in PBS without $Ca^{2+}$ or $Mg^{2+}$ and subcultured on glass coverslips. After 3-4 days in culture cells were washed in PBS then fixed in 4% paraformaldehyde. After three 10 minute washes in PBS cells were permeabilized with 0.02% Triton-X100 in PBS supplemented with 10% goat serum. The cells were then incubated at 4° C., overnight in the presence of 1000 µM cerium nitrate and 1000 µM europium nitrate solution. Cells untreated with either cerium nitrate or europium nitrate were used as a control. After 24 hours coverslips were mounted on slides using Vectashield (Vector Laboratories Ltd, Burlingame, Calif., USA) and examined using a Zeiss laser scanning confocal microscope (LSM 510). The results are shown in FIG. 4.

For in vitro tissue and in vivo experiments, 10- to 12-week-old (25-30 g) C57BL/6J mice (Harlan-Olac, Bicester, UK) were used under appropriate United Kingdom Home Office personal and project licenses and adhered to regulations as specified in the Animals (Scientific Procedures) Act (1986) and according to institutional ethical guidelines.

The mice were killed by decapitation under appropriate anaesthesia. Brains, arteries and blood were removed, rapidly frozen on dry ice and stored at −80° C. for conjugation study. Conjugation of cerium and europium with mouse brain tissue and atherosclerotic tissue was obtained by homogenising 50 mg of tissue in Tris saline buffer (pH7.4) and mixing with different dilutions (1 µM, 10 µM, 100 µM) of the europium nitrate and cerium nitrate. The mixers were kept on a shaker table for 24 hours. The tissue was then mounted onto a slide and coverslipped using Vectashield mounting medium and examined using a Zeiss laser scanning confocal microscope (LSM 510).

Figure 5A:
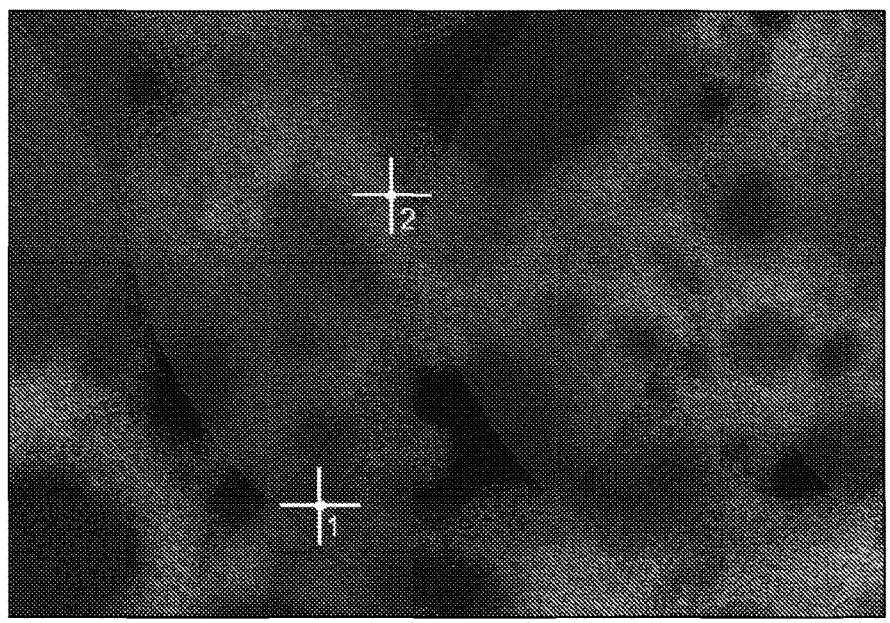
FIG. 5 shows
  (a) confocal image of 100 μM aq europium nitrate mixed with phospholipids when excited with diode laser at 405 nm
  (b) fluorescence emission spectra for 100 μM aq europium nitrate from a confocal image of 100 μM aq europium nitrate mixed with phospholipids when excited with diode laser at 405 nm.
Figure 5B:
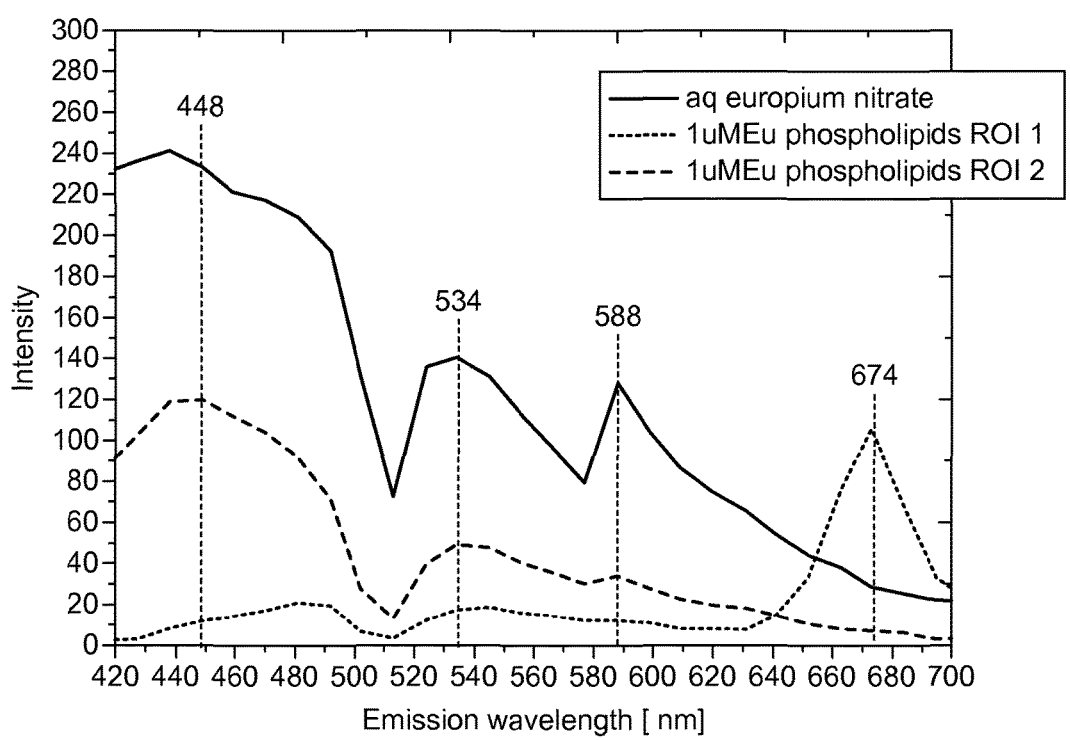

Fluorescence emission spectrum of europium nitrate was obtained by exciting with a diode laser of 405 nm and it gives 3 emissions at 448 nm, 535 nm and 588 nm. Thereafter conjugation of the europium with phospholipids was assessed by first mixing phospholipids with 100 µM europium nitrate analysing under confocal microscope. Two emissions were observed i.e. at 448 nm and 674 nm shown in FIG. 5. Therefore, europium conjugation with phospholipids will give two emission peaks near 448 nm and 674 nm.

Fluorescence Microscopy Results

Brain tissue exposed to 0.1 µM concentration of europium nitrate showed a large number of fluorescent peaks (≥10 peaks in a 100 µm² area) as shown in FIG. 11(a). The white circles indicate $Eu^{3+}$ ions which are conjugated to lipid regions of the brain. This was more than that seen in brain tissue exposed to 1 mM of europium nitrate solution (FIG. 11(b)). The brain tissue controls did not show any evidence of fluorescence under the microscope (FIG. 11(a)).

In Vivo Study

For this 10- to 12-week-old (25-30 g) C57BL/6J mice (Harlan-Olac, Bicester, UK) received intraperitoneal injection of 02. ml of 100 µM europium nitrate in distilled water). After 24 hours mice were perfused transcardially with 0.9% saline followed by 4% paraformaldehyde. Brains, arteries, heart, liver kidneys were removed, post-fixed and 50 m sections were cut on a vibratome (Leica Microsystems, Germany) The sections were mounted on slides, dried at 4° C., cover slipped using vectashield mounting medium and examined using a Zeiss laser scanning confocal microscope (LSM 510).

The confocal image of mouse artery showed some spots with blue emissions.

Fluorescence spectra were obtained and the spectra was compare with aq europium nitrate as shown in the FIG. 8 and similar peak emission are observed which shows that europium is conjugating to the endothelial tissue in artery.

Following intra peritoneal injection of rare earth ions, all the mice appeared completely healthy and behaved normally. For the mice injected with europium nitrate solution, a very low level of europium ions were found to be present in the cardiac and lung, tissue with the highest number of peaks seen in a 100 µm² area being ≤1 for both the heart and lung tissue. The liver tissue showed a much higher concentration of fluorescence than the heart and lung tissue, with the highest number of fluorescent peaks in a 100 µm² area being <10. At higher magnifications it was evident that the europium ions had entered the hepatocytes in the liver tissue. The brain tissue also showed a large amount of fluorescence under the microscope, with the highest number of fluorescent peaks per 100 µm² area being ≥20.

Fluorescence Microscopy Results for In Vivo Study

Figure 10B:
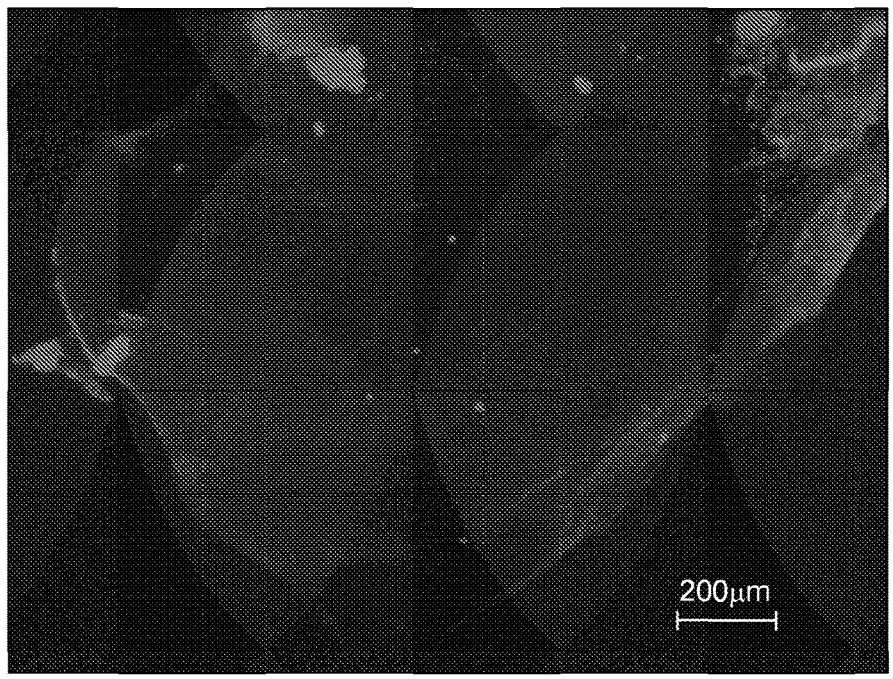

The carotid artery of an atherosclerotic mouse was conjugated with europium nitrate solution (1000 µM) dissolved in Tris saline buffer, mounted onto a slide and a coverslip added using vectashield mounting medium. Sections were viewed on an Axiolmager Z.1 epifluorescence microscope (Carl Zeiss, Welwyn Garden City, UK). FIG. 10(b) shows a fluorescent image with DAPI filter which allows the emission range of 470-500 nm. The white circles seen in FIG. 10(a) indicate the conjugation of the europium with lipid regions of the artery which can be compared to the blue marks in the Fluorescence microscope image shown in FIG. 10(b). Following IP injection of europium and cerium nitrate solution we have found europium and cerium labelling in the brain tissue (FIG. 9) suggesting that these lanthanides cross the blood brain barrier.

The invention claimed is:

1. A method for the measurement of a metabolites in an animal comprising:
    (a) using spectroscopy, detecting a rare earth metal-conjugated marker formed from a rare earth metal conjugated with the metabolite, wherein the spectroscopy is laser spectroscopy or Raman spectroscopy, and wherein the spectroscopy uses an excitation wavelength and a measurement wavelength, each being in the range of about 600 nm to about 2100 nm; and (b) measuring the metabolite based on the detected rare earth metal-conjugated marker.

2. A method according to claim 1 wherein the measured-metabolite correlates with a disease condition.

3. A method according to claim 2 wherein the disease condition is cardiovascular diseases, neuropsychiatric diseases, neurological diseases or cancer.

4. A method according to claim 3 wherein the rare earth metal-conjugated marker is $Eu^{3+}$-conjugated lactic acid.

5. A method according to claim 2 wherein the rare earth metal-conjugated marker is $Eu^{3+}$-conjugated lactic acid.

6. A method according to claim 1 wherein the detecting is non-invasive.

7. A method according to claim 6 wherein the rare earth metal-conjugated marker is $Eu^{3+}$-conjugated lactic acid.

8. A method according to claim 1 wherein the metabolite is
(i) a small molecule metabolite;
(ii) a lipid;
(iii) a peptide;
(iv) a protein; or
(v) an enzyme.

9. A method according to claim 8 wherein the metabolite is:
(i) an amino acid or related compounds selected from taurine, glutamine, N-acetyl-L-asparate (NAA), and homocysteine;
(ii) Lipids and related intermediates selected from phosphatidylcholine and phosphocholine;
(iii) lipid binding proteins selected from lipoprotein A, HDL and LDL;
(iv) Peptides/Proteins selected from PARK 7, Nucleoside Diphosphate Kinase A (NDKA), amyloid beta peptide, Tau (e.g. hyperphosphorylated Tau), CD68, CD64, carcino-embryonic antigen (CEA), tumor-associated glycoprotein 72 (Tag72), folate receptor-α, Alpha actin, Toll-like receptors (TLRs) Creatine, Creatinine, amyloid precursor protein (APP), troponin, C-reactive protein, Fibrinogen and B-type natriuretic peptide (BNP)
(v) Enzymes selected from phospholipases, β-secretase, γ-secretase, succinate dehydrogenase (SDH), fumarate hydratase (FH), neprilysin (NEP), endothelin-converting enzyme (ECE), insulysin (IDE), angiotensin-converting enzyme (ACE) and matrix metalloproteinase 1-9 (MMP 1-9), Creatine kinase (CK) and creatine kinase isoenzyme MB (CKMB)
(vi) Cytokines selected from IL(1-6) and TNFα; or
(vii) small molecule metabolites selected from lactate, glucose, acetyladehyde hydrate, acetate, choline, inositol.

10. A method according to claim 9, wherein the metabolite is lactic acid.

11. A method according to claim 8 wherein the rare earth metal is Cerium, Dysprosium, Erbium, Europium, Gadolinium, Holmium, Neodymium Praseodymium, Samarium, Terbium, Thulium or Ytterbium.

12. A method according to claim 1 wherein the rare earth metal is Cerium, Dysprosium, Erbium, Europium, Gadolinium, Holmium, Neodymium Praseodymium, Samarium, Terbium, Thulium or Ytterbium.

13. A method according to claim 12 wherein the rare earth metal is $Ce^{4+,3+}$, $Yb^{3+}$, $Eu^{3+}$, $Sm^{3+}$, $Tm^{3+}$, $Tb^{3+}$ or $Nd^{3+}$.

14. A method according to claim 13, wherein the rare earth metal is $Eu^{3+}$.

15. A method according to claim 1 wherein the rare earth metal-conjugated marker is $Eu^{3+}$-conjugated lactic acid.

16. A method according to claim 1, wherein a photoluminescence intensity ratio (PLIR) imaging technique is used to calculate the level or a change in level of the metabolite.

* * * * *